United States Patent [19]

Heyden

[11] Patent Number: 4,731,064
[45] Date of Patent: Mar. 15, 1988

[54] URINE DRAINAGE DEVICE WITH ADHESIVE TABS

[76] Inventor: Eugene L. Heyden, S. 627 Bernard # 8, Spokane, Wash. 99204

[21] Appl. No.: 48,993

[22] Filed: Apr. 23, 1987

Related U.S. Application Data

[63] Continuation of Ser. No. 834,560, Feb. 28, 1986, abandoned.

[51] Int. Cl.⁴ .................................................. A61F 5/44
[52] U.S. Cl. ................................. 604/352; 128/132 R
[58] Field of Search ............................... 604/349–353; 128/79, 132 R

[56] References Cited

U.S. PATENT DOCUMENTS

| | | | |
|---|---|---|---|
| 2,604,092 | 7/1952 | Brown et al. | 128/132 R |
| 2,789,560 | 4/1957 | Weimer | 128/295 |
| 3,018,484 | 1/1962 | Koehn | 128/132 R |
| 3,369,546 | 2/1968 | Hickok | 128/295 |
| 3,520,305 | 7/1970 | Davis | 604/349 |
| 3,648,700 | 3/1972 | Warner | 128/294 |
| 3,788,324 | 1/1974 | Lim | 128/295 |
| 3,863,638 | 2/1975 | Rogers III, et al. | 128/295 |
| 4,187,851 | 2/1980 | Hauser | 128/295 |
| 4,378,018 | 3/1983 | Alexander et al. | 128/295 |
| 4,419,097 | 12/1983 | Rowland | 604/352 |
| 4,475,910 | 10/1984 | Conway et al. | 604/349 |

FOREIGN PATENT DOCUMENTS 2016929  9/1979  United Kingdom ................ 604/353

OTHER PUBLICATIONS

"Male Uringary Collection System", Hollister Inc., Libertyville, Illinois 60048.

Primary Examiner—C. Fred Rosenbaum
Assistant Examiner—J. L. Kruter

[57] ABSTRACT

To function as intended, it is desirable that an external or condom catheter be properly applied and maintained upon the penis. An ill-fitting of the device commonly occurs when the catheter is being unrolled during application, and action which tends to push the free end of the penis away from an intended position within the conical body portion of the catheter. Addtionally, an unrolling of the catheter tends to rearwardly displace the relatively loose and relaxed penile skin, causing a displacement of the free end of the penis within the conical body portion once the penile skin returns to its relaxed state. A twisting or kinking of the catheter, leading to outlet obstruction and backflow problems, often results. The solution is one or a plurality of rearwardly or proximally extending flap members emerging preferably from within the conical body portion of the external catheter and adhesively securable to the penis prior to an unrolling the catheter. In the preferred embodiment, an external catheter (10) of suitably flexible material comprises a tubular forward or distal portion (12), an intermediately positioned conical body portion (14), and a thin-walled rearward proximal portion (16) prepaired in an inital rolled up attitude, as is common to the art. Additionally, the catheter comprises a pair of longitudinally extending flap members (24a and 24b) of unitary construction with the device and emerging from fixed locations along the inner surface (18) of the conical body portion. The flap members are provided with an adhesive coating on their inner surface and allow a first attachment of the device to the penis prior to an unrolling the rearward portion thereover. Removable cover slips (28a and 28b) are provided to protect the adhesive surface of each flap member and are removed prior to the application of the device.

14 Claims, 2 Drawing Figures

URINE DRAINAGE DEVICE WITH ADHESIVE TABS

This is a continuation of application Ser. No. 834,560 filed Feb. 2, 1986, now abandoned.

TECHNICAL FIELD

This invention relates to medical devices used in the management of body fluids, and more particularly to external catheters of the condom variety for use with male patients. Representative of such devices are Hickok, U.S. Pat. No. 3,369,546 and Hauser, U.S. Pat. No. 4,187,851.

BACKGROUND ART

It is commonplace in a variety of clinical situations, including reduced levels of consciousness, sequelae to trauma or illness, or advanced age, for patients to lose control of the discharge of urine. It is generally preferable to avoid transurethral catheterization of the urinary bladder as infection, unnecessary discomfort, or internal injury can result. In the male patient, external or condom catheters are useful in this regard.

The external or condom catheter generally comprises an elongated sheath of one-piece construction having a thickened tubular forward portion defining a central fluid passage and connectable to a suitable drainage tube, an intermediately positioned conical body portion having a lesser thickness and providing a forward discharge opening, and a respectively thin-walled rearward portion of a diameter and length sufficient to circumscribe a substantial length of the penis. It is usual for the rearward portion of the catheter to be prepared in an initial rolled up attitude and to be applied to the penis by placing the free end thereof within the conical body portion and then manually unrolling the rearward portion of the catheter over the shaft of the penis.

To secure the catheter in place to the penis after application, and to prevent urine leakage around and beyond its rearward portion, one method employed comprises the application of a spongy adhesive-coated liner pad circumferentially around the shaft of the penis and then an unrolling of a rearward portion of a catheter thereover and beyond the linear pad, as in the Hauser patent.

Another method used to effect an attached relation to the penis and to provide a sealing means is taught by a product similar to the Hickock patent, manufactured by the Mentor Corporation under the name Freedom Cath, and also by a product manufactured by Hollister Incorporated known as The Hollister TM Self-Adhesive Uninary External Catheter. In both the Mentor device and the related Hollister device, the attached and sealing means comprises an adhesive coating applied to the inner surface of the rearward portion of the catheter. When unrolled over the shaft of the penis, the adhesiveness of the rearward portion serves to adhere, in an occlusive manner, directly to the skin of the penis. Found additionally in the Hollister device is an annular and forwardly extending inner flap, existing in the vicinity of the origin of the rearward portion of the device and bonded thereto, which serves exclusively as a seal with the glans of the penis to prevent the backflow of urine.

To function as intended, it is desirable to maintain the free end of the penis in near approximation to the forward discharge opening and within the conical body portion of the external catheter. When properly maintained in such a position, a twisting, collapsing, or kinking of the cathether to a degree which restricts the outflow of urine is prevented. Heretofore, external or condom catheters have been found unsatisfactory in this respect. Often encountered when applying the catheter is a problem which occurs when unrolling the catheter over the penis. Namely, the act of unrolling the rearward portion of the catheter tends to push the free end of the penis away from the forward discharge opening and from a proper position within the conical body portion, contributing to an ill-fitting of the device. Similarly, the relative looseness of the penile skin tends to be pushed ahead of the roll as it is unrolled during application, displacing the skin rearwardly away from a normally relaxed position. After application, i.e. unrolling the catheter, the penile skin will return to a relaxed state and cause the free end of the penis to displace and withdraw from its desired position within the catheter. Additionally, an ill-fitting of the catheter can result from an accidental pulling or stretching of the catheter, effecting a like change in position of the free end of the penis with respect to its forward discharge opening and conical body portion.

DISCLOSURE OF THE INVENTION

The present invention provides a urine drainage device of the external or condom catheter variety with means specific to maintain the intended position of the penis therewithin, preventing malposition thereof which can occur when unrolling of the catheter during application or from actions which pull and stretch the catheter during use. As illustrated in the preferred embodiment of the invention, an external catheter is provided which includes, in a linear continuum, a thickened tubular forward or distal portion providing a central fluid passage and connectable to a drainage tubing, an intermediately positioned conical body portion providing a forward or distal discharge opening, and a respectively thin-walled rearward proximal portion adapted to assume an inital rolled up attitude and of a diameter and length sufficient to cover a substantial length of the penis shaft. Additionally, and according to the preferred embodiment of the invention, a plurality of rearwardly proximally extending flap members extend a suitable length from fixed locations on the inner wall surface of the conical body portion. Meant for a first attachment to the penis, and substantially exposed for ease of application by the rearward portion of the external catheter in an initial rolled up attitude, the flap members are attached directly to the penis prior to unrolling the rearward portion of the catheter thereover. The preferred method effecting attachment between penis and flap member is by an adhesive coating applied directly to the inner surface of the flap member. In keeping with this arrangement, removable cover slips suitably prevents the adhesive-coated surface of each flap member from unwanted adhesive contact with a companion flap member, other catheter members, or with packaging material, and are removed prior to the attachment of the flap members to the penis. Also preferred is an adhesive coating applied to the inner surface of the rearward portion of the catheter which further aids in maintaining an attached relation between the external catheter and the penis, in addition to acting as a seal therewith to prevent leakage from urine backflow.

BRIEF DESCRIPTION OF THE DRAWING

The invention can best be understood in conjunction with the accompanying drawing to which the description of the preferred embodiment corresponds.

BEST MODE OF CARRYING OUT THE INVENTION

Figure 1:
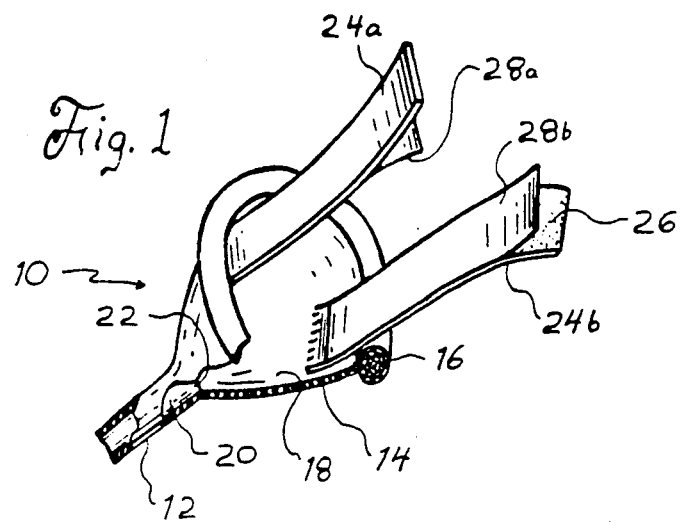
FIG. 1 is a perspective view of the preferred embodiment of the invention, with portions thereof cut away for illustrative purposes.

Referring now to the drawings, and more particularly to FIG. 1 which best illustrates the invention in its preferred construction, the external catheter 10 comprises a generally tubular sheath-like device of elastomer material such as a latex, constructed, as it were, about a longitudinal axis and having a rearward or proximal end and an opposing or distal end. Having in axial alignment a tubular forward or distal portion 12, an intermediately positioned conical body portion 14, and a thin-walled rearward or proximal portion 16 shown in a rolled up state and prior to the application of the device, the external catheter is readily identifiable with external catheters in common usage. Further, the forward portion 12 and the conical body portion 14 respectively define a central fluid passage 20 and an open forward discharge opening 22. The forward distal portion of the external catheter is adapted for connection to a suitable drainage tube (not shown), both of which serve as a conduit for the outward flow of urine from the device. Additionally, and particularly according to the invention, two opposing and rearwardly or proximally extending flap members 24a and 24b of substantially identical character are seen as emerging from fixed locations on the inner wall surface 18 of the conical body portion 14 and comprise an integrally provided extention of the elastomer material common to the remainder of the device. An adhesive coating is applied to the inner surfaces of each flap member, and removable cover slips 28a and 28b are attached thereto, each cover slip in covering relation to each adhesive-coated inner surface. In the figure, cover slips 28a and 28b are shown partially pealed back, exposing to view a part of the adhesive-coated flap surface 26 of inner member 24b. It is to be understood, however, that the cover slips are on optional and convenience feature and, though highly preferred, are not absolutely essential to a practice of the invention.

Preceding further in the description of the invention in its preferred embodiment, the external catheter arrangement, excluding cover slips, is of one-piece construction and of a material having the normal property whereby an increase in thickness thereof reduces its degree of flexibility and a decrease in thickness thereof increases its degree of flexibility. Accordingly, the forward portion 12, the conical body portion 14, as well as flap members 24a and 24b are preferrably of a thickness as to resist undue flexibility. In contrast, the rearward portion 16 is of a very thin and highly flexible nature, lending itself to be easily rolled up and unrolled, and also lending itself to easily and comfortably conform about the penis shaft.

Figure 2:
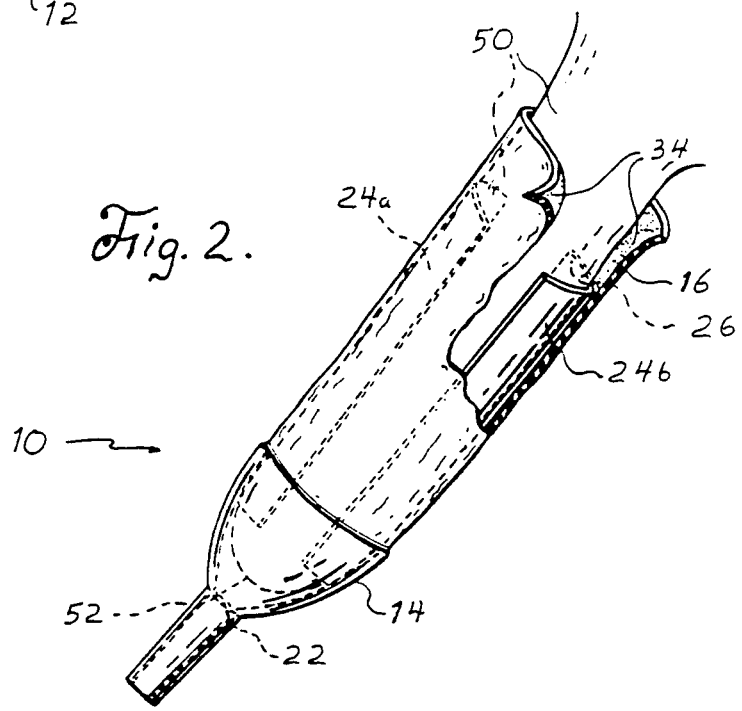
FIG. 2 is a view of the device of FIG. 1, also cut away for illustration, appropriately attached to the penis.

Taken in connection with FIG. 1, FIG. 2 illustrates the external catheter 10 attached, as intended, to the penis shaft 50. With cover slips removed, the external catheter 10 is adhesively attached to the penis shaft by flap members 24a and 24b, and additionally attached to the penis by an extended and contacting rearward portion 16. Accordingly, the catheter can be applied to the penis by first removing the cover slips, placing the free end 52 of the penis within the conical body portion 14 in close approximation to the forward discharge opening 22, attaching flap members 24a and 24b to the penis shaft 50, and then unrolling the rearward portion 16 of the external catheter into its extended position. The adhesive character of the flap members alone may be chosen as the principle means effecting attachment of the device of the penis; however, an adhesive coating applied to portions or all of the inner surface 34 of the rearward portion 16 would coact with flap members for effective attachment of the catheter to the penis, and would further act as a seal when adhesively attached therewith, preventing the backflow of urine past the rearward portion of the device. As an additional consideration, the lengths of the flap members are preferrably less than the extended length of the rearward portion of the external catheter and may be cut to such a length as may be required during their application to a penis of a relatively short longitudinal extent. By allowing a length of the rearward portion of the external catheter to extend beyond the flap members, the likelihood that urine would be directed along an edge of a flap member and past the rearward portion of the catheter would be minimized.

As previously pointed out, a problem particularly addressed by the present invention is the tendency for the free end 52 of the penis to displace from an intended position within the conical body portion 14 as the external catheter is unrolled thereupon. According to the present invention, it can be readily appreciated that, once correctly attached to the penis shaft 50, flap members 24a and 24b act to hold and maintain the free end 52 of the penis in a desired position as the rearward portion 16 is unrolled. It can also be appreciated, after flap member attachment to the penis is achieved, that a degree of traction may be intentionally exerted upon the penis as the rearward portion 16 of the catheter is unrolled, aiding in a smoother application and better fit of the device without appreciably affecting the intended position of the penis within the catheter. Accordingly, if a degree of traction is used during the application of the cathether, and which would forwardly displace the penile skin, it will be seen that the free end 52 of the penis will temporarily withdraw from an intended position near the forward discharge opening 22. However, it will also be seen that the penile skin will return again to a relaxed position once traction is eased, returning the free end of the penis to its intended position with respect to the forward discharge opening. Additionally, it can be appreciated that the flap members will coact with the extended rearward portion of the catheter to lessen the chance that unintentional traction or torsion on the external catheter would urge it from its desired position upon the penis.

INDUSTRIAL CONSIDERATIONS

Though presented in its preferred form, it is to be understood that variations obvious to the principles as herein set forth would be in keeping with the spirit and scope of the invention. Particularly of note is the consideration that, though presented as an integral extention of the material used in the construction of the device, the flap members 24a and 24b may be constructed separately and made unitary with the catheter by a suitable bonding method such as demonstrated by the inner flap arrangement of the aforementioned Hollister device. It would also be in keeping with the present invention to unitarily combine in an external catheter the forwardly extending inner flap feature of the Hollister device with the rearwardly extending flap feature of the present invention. Also of note is the consideration that a provision of only one flap member, or a plurality other than two, would be in keeping with the present invention. Further, it should be noted that, though the self-adhesive feature is regarded as most desirable, it is a consideration in keeping with the invention that a flap member or members may be attached to the penis by other means such as by adhesive tape, or by an encircling, adhesively attached liner pad.

In keeping with the forgoing description of the invention, what is claimed is:

1. A drainage device for managing the discharge of urine when externally applied to a penis, said drainage device having distal and proximal ends and comprising:
   a generally tubular sheath of flexible material presenting a longitudinal axis and a centrally open region therein, said sheath including
   a distal portion of longitudinal extent defining a open central discharge fluid passage,
   a conical body portion emerging from said distal portion and providing a distal discharge opening therein in fluid communication with said open central fluid passage, said conical body portion conically smallest in the vicinity of said distal portion, and
   a proximal portion opposing said distal portion and emerging from said conical body portion and from a conically largest portion thereof, said proximal portion in a rolled up state in a position in the vicinity of said conical body portion and of a dimension adapted to circumferentially cover a substantial length of said penis when unrolled thereupon; and
   at least one longitudinally extending integral flap member means secured to said sheath and having an inner surface and emerging externally from said sheath at an internal location between said distal discharge opening and a location on said proximal portion adjacent said conically largest portion when said proximal portion is in a rolled up state, said flap member means comprising a member of said sheath adapted to extend directionally away from said distal portion and provided to achieve an attached relation to a substantial length of said penis by flap member securing means, so that said flap member means may maintain a penis in the vicinity of said distal discharge opening and within said sheath while said proximal portion is being unrolled to cover a substantial length of said penis.

2. The device of claim 1, wherein said flap member means extends a substantial distance beyond the proximal portion of said sheath when said proximal portion is rolled up and in a position in the vicinity of said conical body portion.

3. The device of claim 2, wherein the length of said flap member means is less than the length of the proximal portion of said sheath.

4. The device of claim 1, wherein said flap member means is flexible and comprises a projection of the flexible material provided in the construction of said sheath.

5. The device of claim 1, wherein said proximal portion is thin and highly flexible with respect to a comparatively thicker and less flexible conical body portion.

6. The device of claim 1, wherein said flap member means has a thickness greater than the thickness of the proximal portion of said sheath whereby said flap member means has a lesser degree of flexibility with respect to the proximal portion of said sheath.

7. The device of claim 1, wherein said flap member means presents an inner surface, and said flap member securing means comprises adhesive means existing on at least a portion of said inner surface of said flap member means.

8. The device of claim 7, wherein a detachable cover slip is carried on the inner surface of said flap member means and substantially covers said adhesive means.

9. The device of claim 1, wherein said flap member means is integrally connected to said conical body portion and is substantially opposed by an additional flap member means of like character.

10. The device of claim 9, wherein said additional flap member means is flexible and comprises a projection of the flexible material provided in the construction of said sheath.

11. The device of claim 9, wherein said additional flap member means has a thickness greater than the thickness of the proximal portion of said sheath whereby said additional flap member means has a lesser degree of flexibility with respect to the same.

12. The device of claim 9, wherein said additional flap member means presents an inner surface, and said flap member securing means comprises adhesive means existing on at least a portion of the inner surface of said additional flap member means.

13. The device of claim 12, wherein a detachable cover slip is carried on the inner surface of said additional flap member means and substantially covers said adhesive means.

14. The device of claim 1, wherein adhesive means exists on a substantial amount of an inner surface of the proximal portion of said sheath whereby said proximal portion may adhesively attach to said penis.

* * * * *

UNITED STATES PATENT AND TRADEMARK OFFICE
CERTIFICATE OF CORRECTION

PATENT NO. : 4,731,064

DATED : Mar. 15, 1988

INVENTOR(S) : Eugene L. Heyden

It is certified that error appears in the above-identified patent and that said Letters Patent is hereby corrected as shown below:

Abstract, line 7, "Addtionally" should be --Additionally--.
         line 22, after "rearward" insert --or--.
         line 29, "surface and allow" should be --surfaces, allowing--.

line 31, after "unrolling" insert --of--.
Col. 1, line 22, place a comma after "bladder".
        line 37, delete "then".
        line 54, "attached" should be --attachment--.
Col. 2, line 1, after "When" insert --this portion of the penis is--.
        line 7, delete "unrolling".
        line 7, after "catheter" insert --is unrolled--.
        line 13, after "tends" insert --to cause the same--.
        line 14, delete "it" and insert --the catheter--.
        lines 14 and 15, delete "during application".
        line 19, "its desired" should be --the intended--.
        line 23, "its" should be --the--.
        line 24, after "portion" insert --of the device--.
        line 32, "when" should be --while--.
        line 32, delete "of".
        line 33, delete "and stretch" and insert --at--.
        line 41, after "rearward" insert --or--.
        line 46, after "rearwardly" insert --or--.
        line 58, "prevents" should be --prevent--.
        line 64, after "catheter" insert --, a feature--.
Col. 3, line 21, after "opposing" insert --forward--.
        line 24, place a comma after "16".
        line 26, after "identifiable" insert --in feature--.
        line 29, after "a" insert --open--.
        line 29, delete "an open" and insert --a--.
        line 30, after "forward" insert --or--.

UNITED STATES PATENT AND TRADEMARK OFFICE
CERTIFICATE OF CORRECTION

PATENT NO. : 4,731,064

DATED : Mar. 15, 1988

INVENTOR(S) : Eugene L. Heyden

It is certified that error appears in the above-identified patent and that said Letters Patent is hereby corrected as shown below:

```
           lines 39 and 40, "an integrally provided" should be --a formed
                    and component--.
           line 47, "flap" should be --inner--.
           line 47, "inner" should be --flap--.
           line 49, "on" should be --an--.
           line 49, place a comma after "feature".
           line 52, "Preceding" should be --proceeding--.
           line 56, delete "thereof".
           line 56, "its" should be --the--.
           line 60, place a comma after "24b".
           line 60, after "of" insert --such--.
Col. 4,    line  2, after "and" (second occurrence) insert --is--.
           line 47, delete "and" and insert --an action--.
           line 58, "its desired" should be --the intended--.
           lines 63 & 64, "variations obvious to the principles as herein
                    set forth would be in keeping with the
                    spirit and scope of the invention" should be
                    --the practice of the invention may be according
                    to variations consistant with its spirit
                    and scope--.
           line 66, "an integral" should be --a formed and component--.
Col. 5,    line 18, "forgoing" should be --fore-
```

Signed and Sealed this

Twenty-seventh Day of June, 1989

Attest:

DONALD J. QUIGG

Attesting Officer

Commissioner of Patents and Trademarks